(12) United States Patent
Andrews et al.

(10) Patent No.: US 6,835,728 B2
(45) Date of Patent: Dec. 28, 2004

(54) DRUG COMBINATION FOR THE TREATMENT OF DEPRESSION AND RELATED DISORDERS COMPRISING MIRTAZAPINE

(75) Inventors: John Stuart Andrews, Schilde (BE); Wilhelmus Drinkenburg, Molenschot (NL); Nicholas Matthew Ward, Scotland (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/181,843

(22) PCT Filed: Jan. 15, 2001

(86) PCT No.: PCT/EP01/00407

§ 371 (c)(1),
(2), (4) Date: Oct. 8, 2002

(87) PCT Pub. No.: WO01/52855

PCT Pub. Date: Jul. 26, 2001

(65) Prior Publication Data

US 2003/0105083 A1 Jun. 5, 2003

(30) Foreign Application Priority Data

Jan. 19, 2001 (NL) .......................................... 00200189

(51) Int. Cl.⁷ ............................................. A61K 31/55
(52) U.S. Cl. .................. 514/214.02; 514/220; 514/922
(58) Field of Search ........................... 514/214.02, 220, 514/922

(56) References Cited

U.S. PATENT DOCUMENTS 5,114,976 A * 5/1992 Norden ........................ 514/646
5,977,099 A * 11/1999 Nickolson ................... 514/214
6,150,353 A * 11/2000 Broekkamp et al. ... 514/214.02

FOREIGN PATENT DOCUMENTS

WO  94 19026 A  1/1994
WO  98 43646 A  8/1998

OTHER PUBLICATIONS

Chemical Abstracts 110:108817, "5–HT1 Agonists Reduce 5–Hydroxytryptamine Release . . . ", Sharp et al (1989).*

Koe B K et al: "Effects of Serotoninergic Agents on Down–regulation of beta–Adrenoceptors by the Selective Serotonin Reuptake Inhibitor Sertraline."; Archives Internationales de Pharmacodynamie et de Therapie, vol. 329, No. 2, 1995, pp. 231–244.

Bailer Ursula et al: "The use of mirtazapine in depressed inpatients." Wiener Klinische Wochenschrift, vol. 110, No. 18, Oct. 2, 1998, pp. 646–650.

Mulrow C.D. et al: "Efficacy of newer medications for treating depression in primary care patients." American Journal of Medicine, (2000), 10/81,(54–64).

Williams J.W. Jr. et al: "A systematic review of newer pharmacotherapies for depression in adults: Evidence report summary." Annals of Internal Medicine, (May 2, 2000), pp. 743–756.

* cited by examiner

Primary Examiner—Frederick Krass
(74) Attorney, Agent, or Firm—Mark W. Milstead

(57) ABSTRACT

The invention relates to a combination comprising an amount of mirtazapine, or a pharmaceutically acceptable salt or solvate thereof, and an amount of gepirone, or a pharmaceutically acceptable salt or solvate thereof, optionally in association with one or more pharmaceutically acceptable carriers, whereby the amount of gepirone and the amount of mirtazapine are such that the effect of the composition is more favourable than the added effects of the amounts of each drug separately. This combination can be used in the treatment of depression and related disorders, whereby the invention also provides for a new method of treatment of depression and related disorders.

2 Claims, No Drawings

DRUG COMBINATION FOR THE TREATMENT OF DEPRESSION AND RELATED DISORDERS COMPRISING MIRTAZAPINE

This application is the National Stage of International Application PCT/EP01/00407, filed Jan. 15, 2001, claims priority to EP 00200189.9, filed Jan. 19, 2000.

FIELD OF THE INVENTION

The invention relates to a combination comprising mirtazapine, to a package containing dosage units comprising mirtazapine, and to a method of treatment of depression and related disorders.

BACKGROUND OF THE INVENTION

Disorders of the central nervous system, such as depression and anxiety are illnesses that affect people of all ages. Although there are many effective drugs available for treatment of these diseases, the currently available methods of treatment are often still not adequate. Most noteworthy is that there are no positive treatment results in about one third of all subjects with depression or anxiety and recovery in the effectively treated group is slow, with an onset of effect at the earliest two weeks after the start of drug treatment.

Mirtazapine (Org 3770; disclosed in U.S. Pat. No. 4,062,848), or the newly introduced drug gepirone (disclosed in U.S. Pat. No. 4,423,049), are examples of modern drugs for the treatments of depression and anxiety with favourable side effect profiles and very low risks for a lethal overdose. For more effective treatment there is hope that the different mechanisms of action of drugs enables complementary use, in the sense that patients not responding to one drug, may turn out to be responsive to another drug. Sometimes, drugs with the same therapeutic indication are prescribed as combination therapy in order to profit from such a mutually supplementary effect although it is generally not recommended to combine antidepressant drugs in view of risks for cumulative side effects or synergistic toxic interactions (Schweitzer and Tuckwell, in Drug Safety, Vol. 19, pp 455–464, 1998). Usually, if a seemingly positive effect of a known drug combination occurs in an individual patient, the positive effect is due to only one of the drugs in the combination. More desirable is a truly synergistic effect of two drugs with the same indication, in the sense that the effect of the combination is superior over an additive effect of the effects of both drugs in an individual patient. There are only very few synergistic therapeutic drug interactions known which have found acceptance in the area of treatment of central nervous system diseases. Most information is available on so-called augmentation therapy of treatment resistant depression by addition of lithium to anti-depressant drugs. The use of such a combination is viewed with caution in view of the side effects of lithium (Hardy et al., Journal Clin. Psychopharmacology, vol. 17, pp 22–26, 1997). The results of a combination of lithium with mirtazapine has been disclosed with favourable results, but the augmentation is not so strong that this combination would be selected as first choice treatment of depressive disorders (Bruijn et al., Journal Clin. Psychiatry, Vol. 59, pp 657–663, 1998).

BRIEF SUMMARY OF THE INVENTION

It is therefore all the more surprising that a synergistic effect is found with mirtazapine and gepirone. This invention provides for a combination comprising an amount of mirtazapine, or a pharmaceutically acceptable salt or solvate thereof, and an amount of gepirone, or a pharmaceutically acceptable salt or solvate thereof, optionally in association with one or more pharmaceutically acceptable carriers, whereby the amount of gepirone and the amount of mirtazapine are such that the effect of the combination is more favourable than the added effects of the amounts of each drug separately. Thus, gepirone and mirtazapine truly have a synergistic interaction when used in the treatment of depression and related disorders. As a consequence, the combined use of mirtazapine and gepirone has better effects in more patients in comparison to each drug alone. The better effect can reside in less side effects or a faster or more complete recovery in individual patients or in the overall result of the treatment of a group of patients. The preferred use of the combination will be in the treatment of the before mentioned treatment-resistant depression, also known as refractory depression or treatment refractory depression.

The present invention thus concerns the administration of two different psychotropic drugs from different pharmacological categories, each drug enhancing the therapeutic efficacy of the other drug in the treatment of depression and related disorders.

The following specifications of the terms used above serve to clarify better what is provided by this invention.

The drug name mirtazapine also refers to the individual (R) and (S) enantiomers of mirtazapine. These can be used as their salts, substantially free, i.e. associated with less than 5%, preferably less than 2%, in particular less than 1% of the other enantiomer or as mixtures of such enantiomers in any proportions including racemic mixtures containing substantially equal amounts of the two enantiomers.

Unless otherwise stated all amounts of the active components refer to the weights of mirtazapine or gepirone as base. According to the terminology in this description the drugs gepirone and mirtazapine are the active ingredients or active components of the combination.

Pharmaceutically acceptable salts include acid addition salts, for example, hydrochloric, fumaric, maleic, citric or succinic acid, these acids being mentioned only by way of illustration and without implied limitation.

The terms pharmaceutically acceptable carriers and excipients refer to those substances known in the art to be allowable as filler or carrier material in pills, tablets, capsules etc. The substances are usually approved for this purpose by health-care authorities and are inactive as pharmacological agents. A compilation of pharmaceutically acceptable carriers and excipients can be found in the Handbook of Pharmaceutical excipients ($2^{nd}$ edition edited by A. Wade and P. J. Weller; Published by the American Pharmaceutical Association, Washington and The Pharmaceutical Press, London in 1994). Specifically, lactose, starch, cellulose derivatives and the like, or mixtures thereof, can be used as carriers for the active components of the combination according to this invention.

DETAILED DESCRIPTION OF THE INVENTION

The term combination refers to any presentation form in which the intention for combined use of mirtazapine and gepirone can be recognised. Such combinations of mirtazapine and gepirone may in this description also be referred to as combinations according to the invention. It will be appreciated that the compounds of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention. For example, a combination can be made suitable by adding instructions or aids or even determinants for the combined use. Determinants for the combined use can, for example, reside in the properties of a dispenser of dosage units of the active ingredients of the combination. The active ingredients can thus be in separate dosage units, but still the combination can have a determinant inducing the use of the dosage units of the combination in a predetermined sequence and/or at pre-determined times by the properties of the dispenser. A preferred determinant for combined use is of course the formulation of both the active components of the combination in one pharmaceutical composition. Thus according to one aspect, the present invention provides a pharmaceutical composition, comprising mirtazapine, or a pharmaceutically acceptable salt or solvate thereof, and gepirone, or a pharmaceutically acceptable salt or solvate thereof.

The effects of mirtazapine and gepirone separately are usually referred to as anti-depressant effects, implying mood improving effects in depressed patients. However the effects of these drugs is not limited to an effect in depressed patients. Certain other diseases and symptoms influenced by the central nervous system are also known to improve by treatment with mirtazapine or gepirone. In more general terms, these drugs have psychotropic activity. This term refers here to any effect on the functioning of the central nervous system, useful to influence behaviour and feelings of well-being of mammals, in particular humans.

The term 'depression and related disorders' refers to a medical field which can be understood by the skilled person by his knowledge of the current use of anti-depressant drugs. Those disorders known to respond positively to treatment with drugs classified as antidepressants are considered for the description of this invention as being related to depression. Such disorders are for example anxiety disorders, such as panic disorder, obsessive compulsive disorder, posttraumatic stress disorder, or chronic pain syndromes. It is well known that anti-depressant drugs have more general beneficial effects on behaviour and mental functioning which is not strictly limited to an effect on depression. Also included in the invention is the use in anxiety in the manner in which anti-depressant drugs are used, that is with extended use for a long term effect, which is to be distinguished from the use of typical anxiolytic drugs, also referred to as minor tranquillisers, which have an acute anxiety relieving and often sedative effect. The latter anxiolytic/sedative effect is usually ascribed to interactions with the GABA-receptor in the brain.

Such pharmacological information can lead to placement of drugs in different categories. Independent from the medical categories 'anxiolytic, 'anti-depressant', 'neuroleptic' etc., or the chemical categories 'tetracyclics', 'benzodiazepines' etc., drugs can be categorised on basis of pharmacological mechanism. In this sense gepirone is often placed in another drug category than mirtazapine. Where the latter is referred to as an '$\alpha_2$-blocker' or 'noradrenergic and selective serotonergic antagonist' ('NASSA'), gepirone is known as a partial 5-$HT_{1A}$-agonist'.

While it is possible for the active ingredients of the combination to be administered as the raw chemical it is preferable to present them as a pharmaceutical composition, also referred to in this context as pharmaceutical formulation. Suitable compositions include those suitable for oral, rectal, nasal, topical (including transdermal, buccal and sublingual), vaginal or parenteral (including subcutaneous, intramuscular, intravenous and intradermal) administration.

Pharmaceutical compositions in embodiments of the present invention comprise mirtazapine or gepirone or a combination thereof together with one or more pharmaceutically acceptable carriers or excipients and optionally other therapeutic agents. The present invention further provides compositions according to the invention for use in therapy of depression and related disorders. Furthermore, the invention includes the use of mirtazapine and gepirone in the manufacture of a medicament comprising mirtazapine and gepirone, having psychotropic activity with improved efficacy for therapy, in particular, of depression and related disorders. This medicament has an enhanced effect or less side effects in comparison to each drug alone. The preferred use of the medicament will be for the treatment of treatment-resistant depression. The invention includes as well the use of mirtazapine and gepirone in the manufacture of medicaments for administration in combination (either concomitantly or sequentially) with gepirone or mirtazapine, respectively, for the treatment of depression or related disorders.

An important aspect of the present invention is that it provides a method for the treatment of an individual of a vertebrate species, for example, a mammal including a human patient, suffering from depression or a related disorder, which method of treatment comprises administering an effective amount of mirtazapine in combination with gepirone. The desired daily doses for a treatment is preferably presented as a single dose or in two, or three sub-doses administered at appropriate intervals throughout the day. In practice this means among others to provide dosage units comprising mirtazapine and dosage units comprising gepirone in a combination or to provide dosage units comprising mirtazapine and gepirone for administration to a recipient or intake by a recipient for treatment.

Thus, in one embodiment of the invention a mixture of mirtazapine and gepirone may be presented as a pharmaceutical formulation in unit dosage form, for example, administered in the form of a tablet, pill, capsule and the like. Such dosage forms are known in the art, e.g. as described in the standard reference, Gennaro et al., Remington's Pharmaceutical Sciences, (18th ed., Mack Publishing Company, 1990, see especially Part 8: Pharmaceutical Preparations and Their Manufacture). By means of pharmaceutically suitable liquids the compounds can also be applied as an injection preparation in the form of a solution, suspension, emulsion, or as a spray, e.g. a nasal spray.

For the preparation of pharmaceutical compositions and more specifically dosing units, the present invention further includes a process for the preparation of a pharmaceutical formulation comprising mirtazapine and gepirone, which process comprises bringing an amount of mirtazapine (or a pharmaceutically acceptable salt thereof) and amount of gepirone (or a pharmaceutically acceptable salt thereof into association with one or more pharmaceutical excipients.

More commonly these days pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions. Thus, the invention further includes a pharmaceutical formulation, as herein before described, in combination with packaging material suitable for said formulations. In such a patient pack the intended use of a formulation for the combination treatment of depression or related disorders can be inferred by instructions, facilities, provisions, adaptations and/or other means to help using the formulation most suitably for the treatment. Such measures make a patient pack specifically suitable for and adapted for use for treatment with the combination of the present invention.

Specifically, a further embodiment includes a package containing separate dosage units, one or more of which containing mirtazapine or a pharmaceutically acceptable salt thereof and one or more of which containing gepirone or a pharmaceutically acceptable salt thereof. A package contains enough tablets, capsules or the like to treat a patient for a pre-determined period of time, for instance for 2 weeks, 1 month or 3 months.

For the use of the combination of the present invention it should provide the active ingredients such that effective amounts for treatment are made available. The amount of a combination of mirtazapine (or a pharmaceutically acceptable salt or solvate thereof) and gepirone (or a pharmaceutically acceptable salt or solvate thereof), required to produce the efficacious effects will, of course, vary and is ultimately at the discretion of the medical practitioner. The factors to be considered include the route of administration and nature of the formulation, the recipient's body weight, age and general condition and the nature and severity of the disease to be treated.

In general, a suitable dose of mirtazapine for administration to a human will be in the range of 0.05 to 5 mg per kilogram body weight of the recipient per day, preferably in the range of 0.1 to 1.0 mg per kilogram body weight per day.

A suitable dose of gepirone for administration to a human will usually be in the range of from 0.01 to 3 mg per kilogram body weight of the recipient per day, preferably in the range of from 0.05 to 0.7 mg per kilogram body weight per day.

The compositions (formulations) according to this invention may be prepared by any methods well known in the art of pharmacy, for example, using methods such as those described in Gennaro et al., Remington's Pharmaceutical Sciences (18th ed., Mack Publishing Company, 1990, see especially Part 8: Pharmaceutical Preparations and their Manufacture). Such methods include the step of bringing into association an active ingredient with a carrier which constitutes one or more accessory ingredients. Such accessory ingredients include those conventional in the art, such as, fillers, binders, diluents, disintegrants, lubricants, colorants, flavouring agents and wetting agents.

Formulations suitable for oral administration may be presented as discrete units such as pills, tablets or capsules each containing a predetermined amount of active ingredient(s); as a powder or granules; as a solution or suspension. The active ingredient(s) may also be present as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

For making dosage units, e.g. tablets, the use of conventional additives such as fillers, colorants, polymeric binders and the like is contemplated. In general any pharmaceutically acceptable additive which does not interfere with the function of the active compounds can be used. Suitable amounts of active ingredients are, for example, a tablet comprising 1 to 50 mg of mirtazapine and typically 1 to 30 mg of gepirone. In a specific example, a tablet comprising 15 mg of mirtazapine and 10 mg of gepirone is obtained.

Mirtazapine may be prepared using the method described in U.S. Pat. No. 4,062,848 which is incorporated herein by reference.

Gepirone may be prepared by any method known in the art. Typically the compound is prepared by the methods described in U.S. Pat. No. 4,423,049. Pharmaceutical compositions containing gepirone are disclosed in U.S. Pat. No. 5,478,572. The contents of these documents are incorporated herein by reference.

The invention is further illustrated by the following examples.

Assays of antidepressant activity were conducted to demonstrate that combining mirtazapine and gepirone can potentiate their antidepressant profile. The assays selected were the defensive or marble burying test in mice and EEG sleep-wake activity (ACSO) test in rats.

EXAMPLE 1

Defensive Burying Test

Marble burying has been developed and validated as a pre-clinical assay of potential anxiolytic activity (Andrews and Broekkamp (1993). Procedures to identify anxiolytic or anxiogenic agents. In *Behavioural Neuroscience*, ed. A Sahgal, pp. 37–54. IRL Press, Oxford). The marble burying test places a naive mouse into a novel environment containing 25 marbles (arranged on top of a saw dust surface). A reduction in the number of marbles buried by the mouse has been hypothesised to be an anxiolytic-like/anti-depressant-like effect.

Gepirone administered alone reduced marble burying with an $ED_{50}$ of 2.16 mg.kg$^{-1}$ with subcutaneous administration (S.C.). Mirtazapine administered alone reduced marble burying with an $ED_{50}$ of 5.5 mg.kg$^{-1}$ S.C. A further series of three separate experiments were conducted during which three single doses of mirtazapine (0.3, 1, 3 mg.kg$^{-1}$) were co-administered S.C. with a range of S.C. gepirone doses (0, 0.1, 0.3, 1, 3 mg.kg$^{-1}$). The co-administration of mirtazapine and gepirone dose dependently reduced the $ED_{50}$ of gepirone as the dose of mirtazapine increased (see Table I).

TABLE I

The effects of combining gepirone and mirtazapine treatments on behaviour in the marble burying test of anxiolytic/antidepressant activity.
Columns indicate treatment regime with pre-treatment time in minutes, doses administered, and calculated $ED_{50}$.

|  | (mg · kg$^{-1}$) | (mg · kg$^{-1}$) mirtazapine | $ED_{50}$ (mg · kg$^{-1}$) Gepirone |
|---|---|---|---|
| Gepirone (−30') | — | 0, 0.3, 1, 3, 10 | 2.16 |
| Mirtazapine (−30') | 0, 2.2, 4.6, 10, 22 | — | 5.5 |
| Gepirone (−30')/Mirtazapine (−40') | 0.3 | 0, 0.1, 0.3, 1, 3 | 0.75 |
| Gepirone (−30')/Mirtazapine (−40') | 1 | 0, 0.1, 0.3, 1, 3 | 0.5 |
| Gepirone (−30')/Mirtazapine (−40') | 3 | 0, 0.1, 0.3, 1, 3 | 0.4 |

EXAMPLE 2

EEG Test

The aim of this test was to characterise the effects on rat sleep-waking behaviour of gepirone alone and of gepirone after co-administration with mirtazapine. To this end additionally the effects of mirtazapine on it own were investigated. Sleep-waking behaviour was analysed by using electroencephalographic (EEG) recordings, electromyographic (EMG) recordings, and by recording a movement index. On the basis of these signals sleep-waking behaviour was automatically classified per 2 second periods into 6 classes: active waking, passive waking, light sleep, deep sleep, intermediate stage sleep and REM sleep (Ruigt et al. A large scale automated system for rat sleep staging. I. Methodology and technical aspects. Electroenceph. and Clin. Neurophysiol.; 1989; 73:52–64). Each experiment is performed simultaneously on 32 adult male Sprague-Dawley rats (Harlan Olac, Bicester, UK, weighing 250–800 g), subdivided into four treatment groups. Throughout the whole experiment the animals stay in recording cages and are only taken out to be injected with vehicle or test compound(s). Each experiment contains three sessions. The first session ("test session"), commencing at 10:00 AM with a variable duration of 2–5 hours, serves as adaptation period and is used to assess the quality of the EEG and EMG signals recorded. The second and third sessions both start at 2:30 PM on two consecutive days and have a duration of 15.5 hours each. At the start of the second session all groups receive a vehicle treatment, at the start of the third session all groups receive their test compound(s). One of the treatment groups usually receives the vehicle treatment in both sessions to serve as a baseline for the other groups in the experiment. Separate experiments were done in which different single I.P. administered doses of either gepirone (1.0, 3.0, 10.0 mg/kg), or mirtazapine (2.2, 4.6, 10 mg/kg), or mirtazapine (2.2 mg/kg) in combination with gepirone (1.0, 3.0, 10 mg/kg) were tested. Gepirone was dissolved in 0.9% NaCl m/v in water (saline); mirtazapine was dissolved in 5% m/v Mulgofen (EL 719, GAF) in saline (=0.9% m/v NaCl in water).

Independently, in a comparable way a large number of reference compounds (Ruigt et al., Computer-based prediction of psychotropic drug classes based on a discriminant analysis of drug effects on rat sleep. Neuropsychobiology; 1993; 28:138–154). from different psychotropic drug classes (antidepressant [AD], antipsychotic [APS], hypnotic [HYP], anxiolytic [AXL], stimulant [STIM], anticonvulsant [AC]) was previously tested at different doses against placebo [PLAC] for their effects on rat sleep-waking behaviour. The effect profiles for these compounds at active doses were subjected to a discriminant analysis over these 6 psychoactive classes with placebo being added as an extra class. The resulting discriminant function was used to predict the pharmaco-therapeutic application area for gepirone alone and after co-administration with mirtazapine.

Results

The drug-induced changes in sleep waking behaviours after I.P. administration of mirtazapine, gepirone, and mirtazapine in combination with gepirone are presented in Tables II, III and IV. Tables list the effects of the tested compounds on several hypnogram parameters used for subsequent drug classification for two subsequent 3-hour periods after treatment and for the 5-hour dark period from 9–14 h after treatment.

TABLE II

Total effects over the period from 0 to 3 hours after drug injection
(Data are expressed as percentage change over control values)

| Drug | mirt | gepir | gepir | gepir | Gepir + mirt | Gepir + mirt | gepir + mirt |
|---|---|---|---|---|---|---|---|
| Dose | 2.2 | 1.0 | 3.0 | 10.0 | 1.0 + 2.2 | 3.0 + 2.2 | 10.0 + 2.2 |
| N (drug/control) | 8/7 | 6/5 | 8/5 | 6/5 | 7/6 | 6/7 | 7/7 |
| Median duration | | | | | | | |
| Active waking | 19 | −58* | −8 | 72 | 29 | −14 | 100 |
| Passive waking | −5 | 13 | 156* | 198 | 22 | 229* | 346* |
| Intermediate sleep | −85* | −11 | −76 | −100* | −97* | −90* | −100* |
| REM sleep | −88* | 4 | −83* | −100* | −85* | −100* | −100* |
| Light sleep | 7 | 23 | 8 | −2 | −3 | −10 | −57* |
| Deep sleep | 13 | −2 | −21 | −63* | 55 | −41* | −93* |
| Latency from time of injection to | | | | | | | |
| Deep sleep | −36 | 24 | 24 | 268 | 34 | 1017 | 632 |
| REM sleep | 27 | 3 | 360* | 673* | 73 | 206 | 504 |

*p < 0.05 (Mann-Whitney U-test)

Finally, the effect profiles of gepirone, mirtazapine, and the combination of gepirone and mirtazapine were calculated on the basis of vectors derived from the changes in sleep-wake organisation as shown in tables above. For each dose, the probability that the compound belongs to one of 7 defined classes was calculated.

These values are given in Table V as probability values and suggest that at 2.2 mg/kg mirtazapine has only a weak anti-depressant profile (22%). Gepirone at 3.0 mg/kg has a very weak antidepressant profile (28%) and behaves as an anxiolytic drug at 10.0 mg/kg (63%).

TABLE III

Effects over the period from 3 to 6 hours after drug injection
(Data are expressed as percentage change over control values)

| Drug Org code | mirt | gepir | gepir | gepir | gepir + mirt | Gepir + mirt | gepir + mirt |
|---|---|---|---|---|---|---|---|
| Dose | 2.2 | 1.0 | 3.0 | 10.0 | 1.0 + 2.2 | 3.0 + 2.2 | 10.0 + 2.2 |
| N (drug/control) | 8/7 | 6/5 | 8/5 | 6/5 | 7/6 | 6/7 | 7/7 |
| Median duration | | | | | | | |
| Active waking | 68 | 6 | 30 | −18 | 36 | −8 | 160* |
| Passive waking | 17 | 5 | 13 | −40 | 10 | −2 | 4 |
| Intermediate sleep | −74* | 32 | 64* | 56 | −63 | 9 | −76 |
| REM sleep | −52* | 20 | −3 | −50* | −2 | −13 | −99* |
| Light sleep | 10 | 8 | −2 | 35 | −16 | 3 | −25 |
| Deep sleep | 19 | −5 | −6 | −19 | 35 | 5 | 49 |

*p < 0.05 (Mann-Whitney U-test)

TABLE IV

Effects over the period from 9 to 15 hours after drug injection
(Data are expressed as percentage change over control values)

| Drug | mirt | gepir | gepir | gepir | gepir + mirt | Gepir + mirt | gepir + mirt |
|---|---|---|---|---|---|---|---|
| Dose | 2.2 | 1.0 | 3.0 | 10.0 | 1.0 + 2.2 | 3.0 + 2.2 | 10.0 + 2.2 |
| N (drug/control) | 8/7 | 6/5 | 8/5 | 6/5 | 7/6 | 6/7 | 7/7 |
| Median duration | | | | | | | |
| Active waking | −16 | −16 | −37* | −23* | 2 | −33 | −33 |
| Passive waking | −8 | 38 | 55 | 7 | −24 | −57 | −57 |
| Intermediate sleep | 111 | −2 | 36 | 108* | −26 | 256 | 256 |
| REM sleep | 22 | −12 | 40 | 64 | 40 | 47* | 47* |
| Light sleep | 27 | 14 | 67 | 23 | 1 | −26* | −26* |
| Deep sleep | 20 | 2 | −7 | −5 | −4 | 124* | 124* |

*p < 0.05 (Mann-Whitney U-test)

However, gepirone at 3.0 mg/kg in combination with 2.2 mg/kg mirtazapine, scores clearly as an antidepressant already with a high probability of 68% (see numbers in bold face in table V). At 10.0 mg/kg the combination scores as an antidepressant (46%) with possible stimulant (32%) and anxiolytic (22%) properties.

TABLE V

Classification of the effects of tested compounds (mirtazapine, gepirone) into seven different classes by using a discriminant analysis procedure trained with a number of established reference compounds in the various classes. Probability score in percentage is given for each therapeutic class.

| | Dose (mg/kg) | AD | APS | STIM | AXL | HYP | AC | PLAC |
|---|---|---|---|---|---|---|---|---|
| Placebo | | 0 | 6 | 2 | 0 | 18 | 15 | 11 | 50 |
| Mirtazapine | 2.2 | 22 | 3 | 0 | 20 | 29 | 9 | 16 |
| Placebo | | 0 | 16 | 2 | 0 | 25 | 14 | 10 | 34 |
| Gepirone | 1.0 | 1 | 31 | 0 | 6 | 20 | 7 | 35 |
| | 3.0 | 28 | 14 | 0 | 15 | 9 | 29 | 6 |
| | 10.0 | 16 | 3 | 12 | 63 | 0 | 6 | 0 |
| Placebo | | 0 | 3 | 2 | 0 | 25 | 13 | 9 | 48 |

TABLE V-continued

Classification of the effects of tested compounds (mirtazapine, gepirone) into seven different classes by using a discriminant analysis procedure trained with a number of established reference compounds in the various classes. Probability score in percentage is given for each therapeutic class.

| | Dose (mg/kg) | AD | APS | STIM | AXL | HYP | AC | PLAC |
|---|---|---|---|---|---|---|---|---|
| Mirtazapine + Gepirone | 2.2 + 1.0 | 47 | 0 | 2 | 15 | 11 | 11 | 14 |
| | 2.2 + 3.0 | 68 | 0 | 0 | 26 | 0 | 5 | 0 |
| | 2.2 + 10.0 | 46 | 0 | 32 | 22 | 0 | 0 | 0 |

Key: AD = antidepressant; APS = antipsychotic; STIM = stimulant; HYP = hypnotic; AXL = anxiolytic; AC = anticonvulsant; PLAC = placebo

CONCLUSION

The combination of gepirone and mirtazapine reduced the $ED_{50}$ for marble burying and increased the EEG antidepressant classification beyond the simple additive effect predicted by single administration and thus demonstrates a synergistic action for the combined treatment.

What is claimed is:

1. A method for the treatment of depression in an individual of a vertebrate species in need thereof, comprising administering to said individual an effective amount of mirtazapine in combination with an effective amount of gepirone, wherein said combination has an antidepressant effect which is greater than additive.

2. The method according to claim 1, wherein the effective amount of mirtazapine for administration is about 0.05 to 5 mg per kilogram body weight of the individual per day, and the effective amount of gepirone for administration is about 0.01 to 3 mg per kilogram body weight of the individual per day.

* * * * *